(12) United States Patent
Perkins (10) Patent No.: US 9,229,126 B2
(45) Date of Patent: Jan. 5, 2016

(54) SPATIAL HETERODYNE INTEGRATED COMPUTATIONAL ELEMENT (SH-ICE) SPECTROMETER

(75) Inventor: David L. Perkins, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/428,270

(22) PCT Filed: Sep. 13, 2012

(86) PCT No.: PCT/US2012/055167
§ 371 (c)(1),
(2), (4) Date: Mar. 13, 2015

(87) PCT Pub. No.: WO2014/042642
PCT Pub. Date: Mar. 20, 2014

(65) Prior Publication Data
US 2015/0247950 A1 Sep. 3, 2015

(51) Int. Cl.
*G01B 9/02* (2006.01)
*G01J 3/45* (2006.01)
(Continued)

(52) U.S. Cl.
CPC . *G01V 8/00* (2013.01); *E21B 49/08* (2013.01); *G01N 21/31* (2013.01); *G01N 33/0009* (2013.01); *G01N 33/28* (2013.01)

(58) Field of Classification Search
CPC .......... G01V 8/00; E21B 49/08; G01N 21/31; G01N 33/0009; G01N 33/28
USPC ....................................................... 356/451
See application file for complete search history.

(56) References Cited

U.S. PATENT DOCUMENTS 5,059,027 A * 10/1991 Roesler et al. ................. 356/456
6,351,307 B1 2/2002 Erskine
(Continued)

FOREIGN PATENT DOCUMENTS

| WO | 2011/063086 | 5/2011 |
| WO | 2011/079323 | 6/2011 |
| WO | 2014/042642 | 3/2014 |

OTHER PUBLICATIONS

PCT International Preliminary Report on Patentability, dated Feb. 24, 2014, Appl No. PCT/US2012/055167, "Spatial Heterodyne Integrated Computational Element (SH-ICE) Spectrometer", filed Sep. 13, 2012.

(Continued)

*Primary Examiner* — Gregory J Toatley
*Assistant Examiner* — Hina F Ayub
(74) *Attorney, Agent, or Firm* — Krueger Iselin LLP; Benjamin Fite (57) ABSTRACT

A spatial heterodyne spectrometer may employ an integrated computational element (ICE) to obtain a measure of one or more fluid properties without requiring any moving parts, making it particularly suitable for use in a downhole environment. One illustrative method embodiment includes: directing light from a light source to illuminate a sample; transforming light from the sample into spatial fringe patterns using a dispersive two-beam interferometer; adjusting a spectral weighting of the spatial fringe patterns using an integrated computation element (ICE); focusing spectral-weight-adjusted spatial fringe patterns into combined fringe intensities; detecting the combined fringe intensities; and deriving at least one property of the sample.

28 Claims, 5 Drawing Sheets

(51) Int. Cl.
    *G01V 8/00* (2006.01)
    *G01N 21/31* (2006.01)
    *G01N 33/28* (2006.01)
    *G01N 33/00* (2006.01)
    *E21B 49/08* (2006.01)

(56) References Cited

U.S. PATENT DOCUMENTS

| | | |
|---|---|---|
| 7,330,267 B1 | 2/2008 | Weitzel |
| 7,511,819 B2 | 3/2009 | DiFoggio |
| 7,535,572 B2 | 5/2009 | Englert |
| 7,694,734 B2 | 4/2010 | DiFoggio et al. |
| 7,911,605 B2 | 3/2011 | Myrick et al. |
| 2006/0055935 A1 | 3/2006 | Cheben et al. |
| 2007/0200663 A1 | 8/2007 | White et al. |
| 2008/0221711 A1 | 9/2008 | Trainer |
| 2012/0050750 A1 | 3/2012 | Hays et al. |

OTHER PUBLICATIONS

PCT International Search Report and Written Opinion, dated Nov. 29, 2012, Appl No. PCT/US2012/055167, "Spatial Heterodyne Integrated Computational Element (SH-ICE) Spectrometer", filed Sep. 13, 2012.

Englert, Christoph R. et al., "Spatial Heterodyne Spectroscopy for Long-Wave Infrared: First Measurements of Broadband Spectra", Optical Engineering, vol. 48(10), 105602 (Oct. 2009), 9 pgs.

Harlander, John M., et al., "Robust Monolithic Ultraviolet Interferometer for the SHIMMER Instrument on STPSat-1", Applied Optics, vol. 42, No. 15, p. 2829-2834, May 20, 2003.

* cited by examiner

FIG. 6A  $\lambda_0$

FIG. 6B  $\lambda_1 = \lambda_0 + \delta\lambda$

FIG. 6C  $\lambda_2 = \lambda_0 + 2\delta\lambda$

FIG. 6D  $\lambda_n = \lambda_0 + n\delta\lambda$

SPATIAL HETERODYNE INTEGRATED COMPUTATIONAL ELEMENT (SH-ICE) SPECTROMETER

BACKGROUND

Modern oil field operators demand access to a great quantity of information regarding the parameters and conditions encountered downhole. Such information typically includes characteristics of the earth formations traversed by the borehole and data relating to the size and configuration of the borehole itself. The collection of information relating to conditions downhole, which commonly is referred to as "logging," can be performed by several methods including wireline logging, "logging while drilling" (LWD), and tubing-conveyed logging.

In wireline logging, a probe or "sonde" is lowered into the borehole after some or all of the well has been drilled. The sonde hangs at the end of a long cable or "wireline" that provides mechanical support to the sonde and also provides an electrical connection between the sonde and electrical equipment located at the surface of the well. In accordance with existing logging techniques, various parameters of the earth's formations are measured and correlated with the position of the sonde in the borehole as the sonde is pulled uphole.

In LWD, the drilling assembly includes sensing instruments that measure various parameters as the formation is being penetrated, thereby enabling measurements of the formation while it is less affected by fluid invasion. While LWD measurements are desirable, drilling operations create an environment that is generally hostile to electronic instrumentation, telemetry, and sensor operations.

Tubing-conveyed logging, like wireline logging, is performed in an existing borehole. Unlike wireline logging, tubing-conveyed logging enables a logging tool to travel where a wireline-suspended tool cannot, e.g., in a horizontal or ascending borehole. Tubing-conveyed logging tools typically suffer from restricted communications bandwidths, meaning that acquired data is generally stored in memory and downloaded from the tool when the tool returns to the surface.

In these and other logging environments, measured parameters are usually recorded and displayed in the form of a log, i.e., a two-dimensional graph showing the measured parameter as a function of tool position or depth. In addition to making parameter measurements as a function of depth, some logging tools also provide parameter measurements as a function of azimuth. Such tool measurements have often been displayed as two-dimensional images of the borehole wall, with one dimension representing tool position or depth, the other dimension representing azimuthal orientation, and the pixel intensity or color representing the parameter value.

Once a borehole has been drilled, operators often wish to perform downhole formation testing before finalizing a completion and production strategy. Fluid sampling tools enable operators to draw fluid (i.e., gas or liquid) samples directly from the borehole wall and measure contamination levels, compositions, and phases, usually based on the properties (e.g., optical properties, electrical properties, density, NMR, and PVT properties) of the materials drawn into the sample chamber. Existing downhole fluid analysis tools may have a limited reliability due to, e.g., insufficient instrumentation to perform in-situ analysis, or conversely, too many moving parts.

BRIEF DESCRIPTION OF THE DRAWINGS

Accordingly, there are disclosed in the drawings and detailed description specific embodiments of methods, systems, and downhole tools that employ spatial heterodyne integrated computational element ("SH-ICE") spectrometers. In the drawings.

It should be understood, however, that the specific embodiments given in the drawings and detailed description do not limit the disclosure. On the contrary, they provide the foundation for one of ordinary skill to discern the alternative forms, equivalents, and modifications that are encompassed in the scope of the appended claims.

DETAILED DESCRIPTION

Figures 1, 2:
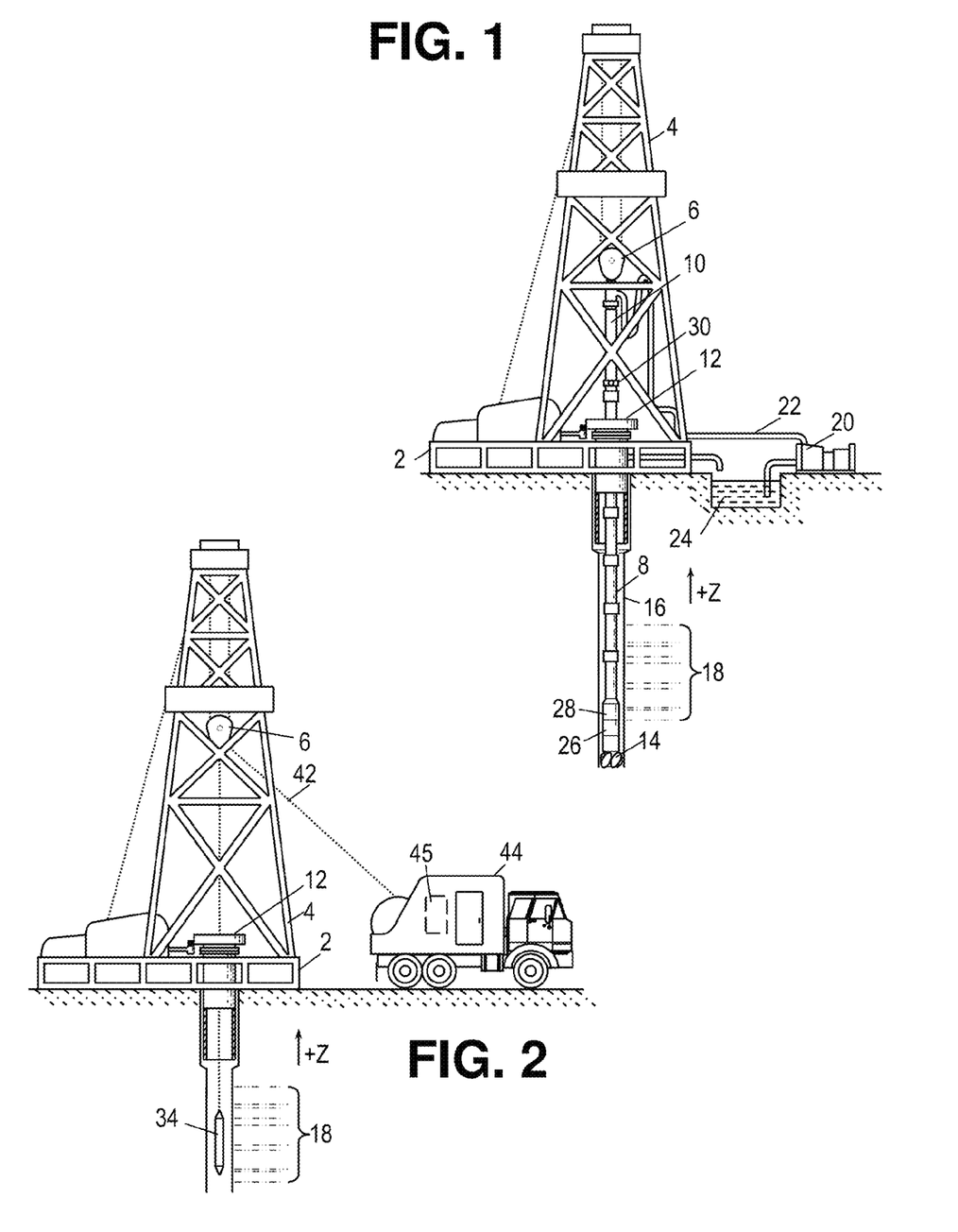
FIG. 1 shows an illustrative environment for logging while drilling ("LWD").
FIG. 2 shows an illustrative environment for wireline logging.

Various systems and methods for performing optical analysis with combined spatial-heterodyne ("SH") integrated computational element ("ICE"), or "SH-ICE" spectrometer, Light from a light source encounters a material to be analyzed, such as a formation fluid sample, a borehole fluid sample, a core sample, or a portion of the borehole wall. The encounter can take various forms, including transmission (attenuation) through the sample, reflection from the sample, attenuated total reflectance (evanescent wave), scattering from the sample, and fluorescence excitation. In any event, the spectral characteristics of the material are imprinted on the light beam and can be readily analyzed with the spectrometer to obtain a measure of characteristics of the substance such as concentrations of selected components. The disclosed spectrometer is believed to be capable of laboratory-quality measurements in a wide range of contexts including a hostile downhole environment, Context The disclosed systems and methods are best understood in the context of the larger systems in which they might be employed. FIG. 1 shows an illustrative logging while drilling (LWD) environment. A drilling platform 2 supports a derrick 4 having a traveling block 6 for raising and lowering a drill string 8. A kelly 10 supports the drill string 8 as it is lowered through a rotary table 12. A drill bit 14 is driven by a downhole motor and/or rotation of the drill string 8. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus around drill string 8, and into a retention pit 24. The drilling fluid transports cuttings from the borehole 16 into the pit 24 and aids in maintaining the integrity of the borehole.

A LWD tool 26 is integrated into the bottom-hole assembly near the bit 14. As the bit extends the borehole 16 through the formations 18, logging tool 26 collects measurements relating to various formation properties as well as the tool orientation and various other drilling conditions. The logging tool 26 may take the form of a drill collar, i.e., a thick-walled tubular that provides weight and rigidity to aid the drilling process. As explained further below, tool assembly 26 includes a optical fluid analysis tool that monitors wellbore fluid properties. A telemetry sub 28 may be included to transfer measurement data to a surface receiver 30 and to receive commands from the surface. In some embodiments, the telemetry sub 28 does not communicate with the surface, but rather stores logging data for later retrieval at the surface when the logging assembly is recovered.

At various times during the drilling process, the drill string 8 may be removed from the borehole as shown in FIG. 2, Once the drill string has been removed, logging operations can be conducted using a wireline logging tool 34, i.e., a sensing instrument sonde suspended by a cable 42 having conductors for transporting power to the tool and telemetry from the tool to the surface, A wireline logging tool 34 may have pads and/or centralizing springs to maintain the tool near the axis of the borehole as the tool 34 is pulled uphole. As explained further below, tool 34 can include a formation fluid sampler that extends a probe against a borehole wall to draw fluids into a sample analysis chamber. A surface logging facility 44 collects measurements from the logging tool 34, and includes a computer system 45 for processing and storing the measurements gathered by the logging tool.

Figure 3:
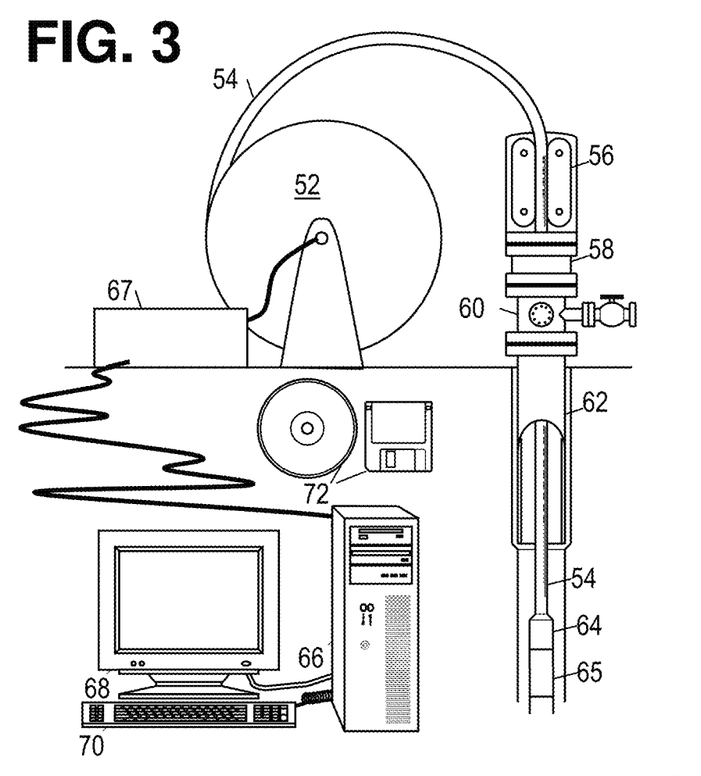
FIG. 3 shows an illustrative environment for tubing-conveyed logging.

An alternative logging technique is logging with coil tubing. FIG. 3 shows an illustrative coil tubing-conveyed logging system in which coil tubing 54 is pulled from a spool 52 by a tubing injector 56 and injected into a well through a packer 58 and a blowout preventer 60 into the well 62. (It is also possible to perform drilling in this manner by driving a drill bit with a downhole motor.) in the well, a supervisory sub 64 and one or more logging tools 65 are coupled to the coil tubing 54 and optionally configured to communicate to a surface computer system 66 via information conduits or other telemetry channels. An uphole interface 67 may be provided to exchange communications with the supervisory sub and receive data to be conveyed to the surface computer system 66.

Surface computer system 66 is configured to communicate with supervisory sub 64 during the logging process or alternatively configured to download data from the supervisory sub after the tool assembly is retrieved. Surface computer system 66 is preferably configured by software (shown in FIG. 3 in the form of removable information storage media 72) to process the logging tool measurements (including the fluid component measurements described further below). System 66 includes a display device 68 and a user-input device 70 to enable a human operator to interact with the system software 72.

In each of the foregoing logging environments, the logging tool assemblies preferably include a navigational sensor package that includes directional sensors for determining the inclination angle, the horizontal angle, and the rotational angle (a.k.a. "tool face angle") of the bottom hole assembly. As is commonly defined in the art, the inclination angle is the deviation from vertically downward, the horizontal angle is the angle in a horizontal plane from true North, and the tool face angle is the orientation (rotational about the tool axis) angle from the high side of the wellbore. In accordance with known techniques, wellbore directional measurements can be made as follows: a three axis accelerometer measures the earths gravitational field vector relative to the tool axis and a point on the circumference of the tool called the "tool face scribe line". (The tool face scribe line is typically drawn on the tool surface as a line parallel to the tool axis.) From this measurement, the inclination and tool face angle of the logging assembly can be determined, Additionally, a three axis magnetometer measures the earth's magnetic field vector in a similar manner. From the combined magnetometer and accelerometer data, the horizontal angle of the logging assembly can be determined.

Figure 4:
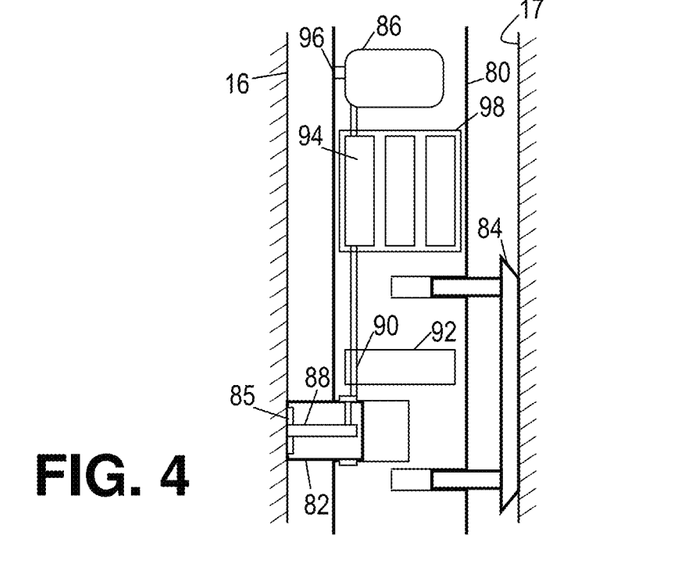
FIG. 4 shows an illustrative formation fluid sampling tool.

FIG. 4 shows an illustrative formation fluid sampler tool 80. Tool 80 can be a drill collar, a coil tubing joint, or a drilling tubular, but most commonly it is expected to be part of a wireline sonde. Tool 80 extends a probe 82 and a foot 84 to contact the borehole wall 17, typically driving them outward from the tool body using hydraulic pressure. The probe 82 and foot 84 cooperate to seat the probe 82 firmly against the borehole wall 17 and establish a seal that keeps borehole fluids from being drawn into the tool 80. To improve the seal, the wall-contacting face of the probe 82 includes an elastomeric material 85 that conforms to the borehole wall 17. A pump 86 draws down the pressure, prompting fluid to flow from the formation through a probe channel 88, a sample chamber 90 in fluid analyzer 92, and a sample collection chamber 94. The pump 86 exhausts fluid into the borehole 16 through a port 96 and continues pumping until a sampling process is completed. Typically, the sampling process continues until the tool 80 determines that the sample collection chamber 94 is full and any contaminants have been exhausted. Thereafter the sample collection chamber 94 is sealed and the probe 82 and foot 84 are retracted. If desired, the tool 80 can repeat the process at different positions within the borehole 16. Sample collection chamber 94 may be one of many such sample collection chambers in a cassette mechanism 98, enabling the tool 80 to return many fluid samples to the surface.

Spatial-Heterodyne Integrated Computational Element Spectrometer

Figure 5A:
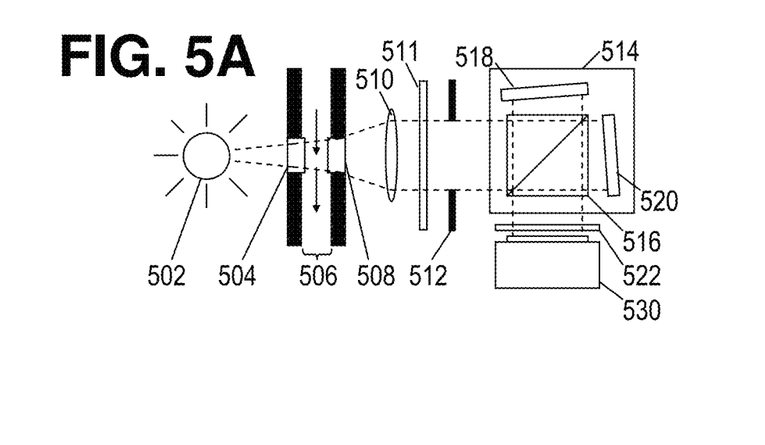
FIGS. 5A-5C show illustrative embodiments of a SH-ICE spectrometer based fluid analyzer.
Figure 5B:
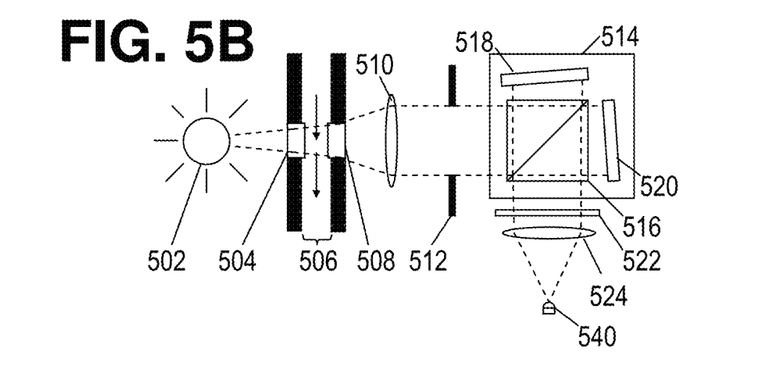
Figure 5C:
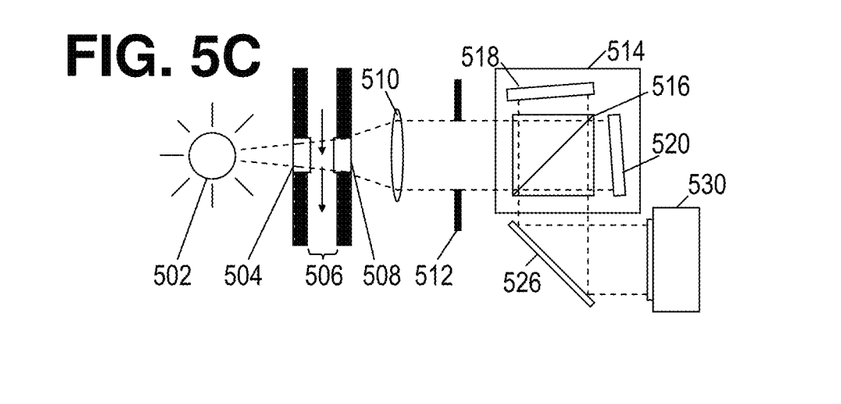

FIGS. 5A-5C show illustrative embodiments of a SH-ICE spectrometer based fluid analyzer. In FIG. 5A, a light source 502 shines light through an inlet window 504 into a sample (shown here as fluid flow stream 506). The light source 502 can he either broadband or narrowband. For the purposes of this disclosure, the term "broadband" is used to distinguish from narrowband sources that provide only isolated peaks in their spectrum. The broadband sources contemplated for use downhole have continuous spectrums in the range of 200-400 nm (for UV absorption and fluorescence spectroscopy), 1500-2300 nm (for special purpose spectroscopy, e.g. GOR (gas to oil ratio) determination), and 400-6000 nm (for general purpose VIS-IR spectroscopy), These examples are merely illustrative and not limiting. One readily available source suitable for this purpose is a tungsten-halogen incandescent source with a quartz envelope, generating light across the 300-3000 nm range. Arc lamps, broadband fluorescent sources, broadband quantum light sources, or a combination of a number of relatively narrowband light sources (such as LEDs) may also be suitable light sources. Suitable narrowband light sources are lasers and single wavelength LEDs, Such narrowband light sources may be used for single wavelength excitation spectroscopy (e.g. Raman and Fluorescence).

The illustrated sample is a fluid flow stream 506 sandwiched between the inlet window 504 and an outlet window 508. Windows 504 and 508 are made from a transparent material (e.g., quartz, diamond, sapphire, zinc selenide) so that the main effect on the spectrum of the light is produced by attenuation as the light passes through the fluid flow stream 506 (i.e., transmission spectroscopy). Other spectrometer configurations may cause the light to interact with the sample (which, in some tool configurations, may be a surface of a solid) via reflection, diffuse reflection, attenuated total reflectance, scattering, or fluorescence. Conversely, some spectrometer embodiments cause the light to pass multiple times through the sample to increase the transmission-induced attenuation.

The light from the sample chamber may captured by a collimation element such as a mirror or lens 510. Spectrometer embodiments employing a narrowband source would typically include a notch filter 511 to block the central frequency emitted by the light source 502 to prevent the intensity at this wavelength from overwhelming the measurements at nearby frequencies, The notch filter 511 can be positioned anywhere on the optical path after the sample (e.g., fluid flow stream 506).

One or more apertures 512 may be positioned at various points along the optical path to define the light into a beam and limit the effects of the beam periphery. A dispersive two-beam interferometer 514 employs a beam splitter 516 to split the incoming light beam into two beams that travel along first and second optical paths before being recombined by the beam splitter 516 into an outgoing beam. (A 50/50 splitter is preferred, but not required.)

Light traveling along the first path interacts with a diffraction grating 518 or other dispersive element that reflects the light at an angle that is dependent on its wavelength, in other words, the beam that returns to the splitter has the spectral components propagating with wavelength-dependent wavefront angles. Similarly, the light traveling along the second path interacts with a second diffraction grating 520 or other dispersive element that produces a return beam with spectral components propagating with wavelength-dependent wavefronts angles. The dispersive elements 518, 520 are positioned to provide the opposite wavefront angles. As the outgoing beam reaches a detector 530, the difference in propagation angles produces a set of interference fringes. As explained below with reference to FIGS. 6A-6E (taken from Roesler, U.S. Pat. No. 5,059,027, "Spatial Heterodyne Spectrometer and Method"), the fringes vary based on the wavefront angle.

Figure 6A:
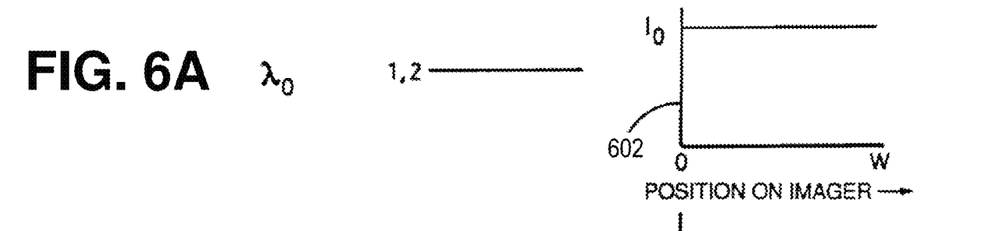
FIGS. 6A-6D illustrate a wavelength-to-spatial fringe relationship.
Figure 6B:
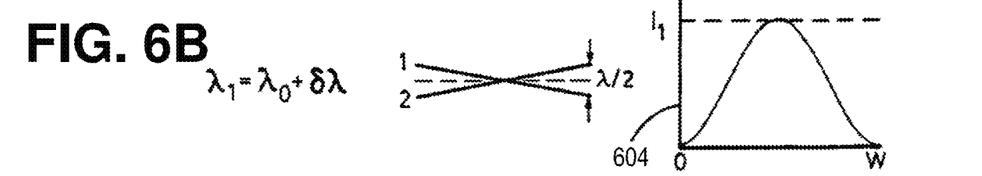
Figure 6C:
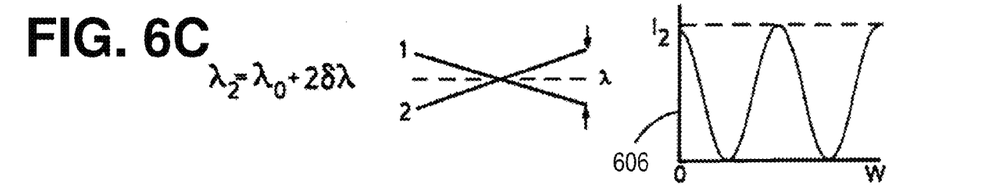
Figure 6D:
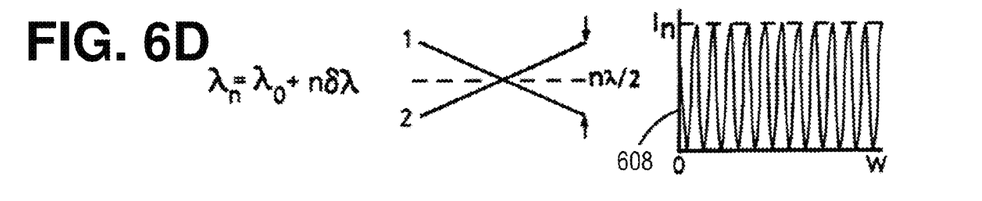
Figure 6E:
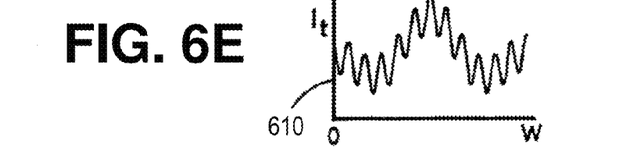
FIG. 6E shows an illustrative combined spatial fringe intensity.

For a baseline or reference wavelength $\lambda_0$, the wavefront angles in both beams are aligned, producing no fringes as indicated in FIG. 6A, Graph 602 shows that the intensity as a function of position on a detector (e.g., detector 530 in FIG. 5A) is constant at this wavelength. As the wavelength increases, the wavefront angles of the two beams become increasingly different. FIG. 6B shows the wavefronts at an angle that produces one fringe on the detector (the intensity variation in graph 604 results when the path difference between the wavefronts varies from $-\lambda/2$ on one edge of the detector to $+\lambda//2$ on the other edge). FIG. 6C shows the wavefronts at an angle that produces two fringes on the detector (the intensity variation in graph 606 results when the phase difference between the wavefronts varies from $-\lambda$ to $+\lambda$. As indicated in FIG. 6D, each increment of the wavelength by a value $\delta\lambda$ adds one fringe across the width of the detector. (Graph 608 shows n fringes across the width of the detector.)

FIGS. 6A-6D illustrate examples of what occurs when only a single wavelength is present. When multiple wavelengths are present, the intensity vs. position relationship becomes more complex, as indicated by graph 610 in FIG. 6E. Nevertheless, a spatial Fourier transform can separate out the contributions from the individual wavelengths.

Figure 6F:
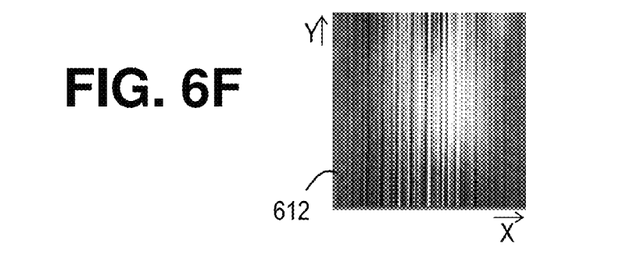
FIG. 6F shows an illustrative spatial fringe image.

The actual image cast by the outgoing beam on the detector is two dimensional. FIG. 6F (excerpted from a figure in N. Gromer et al., "Raman spectroscopy using a spatial heterodyne spectrometer: proof of concept", Appl. Spectroscopy v65, n8, 2011) shows an illustrative two dimensional image 612. Along the width of the detector (i.e., in the x-dimension), the image demonstrates a complex fringe dependence, whereas along the height of the detector (i.e., in the y-dimension) the intensity is relatively constant. The signal-to-noise ratio may be improved by summing or averaging the columns of the image together before analyzing the fringe structure.

Returning to FIG. 5A, the foregoing discussion neglects the presence of element 522, which as explained in greater detail below, is an integrated computation element (ICE) that modifies the outgoing beam image before it strikes detector 530. The ICE 522 is included to exploit the observation that, in addition to spatial intensity variation, the image also contains wavelength-dependent intensity ("color") variation, enabling further processing to be done on the image before it is captured by the detector 530.

The ICE 522 operates to weight the various spectral components of the outgoing light beam by corresponding amounts, the weighting template being chosen based on what fluid properties are being measured. Many ICE implementations are known and potentially suitable, including a transparent substrate carrying a multilayered stack of materials having contrasting refractive indices, e.g., silicon and silica, niobium and niobia, germanium and germania, MgF and SiO. Suitable substrates may include BK-7 optical glass, quartz, sapphire, silicon, germanium, zinc selenide, zinc sulfide, various polymers (e.g., polycarbonates, polymethylmethacrylate, polyvinylchloride), diamond, ceramics, and the like. A transparent protective layer may further be provided over the layers with contrasting refractive indices. The relative weightings of different wavelengths are achieved through a judicious selection of the number, arrangement, and thicknesses of the layers to provide various degrees of optical interference at selected transmitted (or reflected) wavelengths. Other illustrative ICE implementations achieve the wavelength-dependent weightings by suitably varying their transmissivity, reflectivity, absorptivity, dispersivity, and/or scattering properties. Such implementations may employ engineered materials, holographic optical elements, gratings, acousto-optic elements, magneto-optic elements, electro-optic elements, light pipes, and digital light processors (DLPs) or other types of micro-electronic mechanical (MEMs) based light manipulation devices.

Figure 7A:
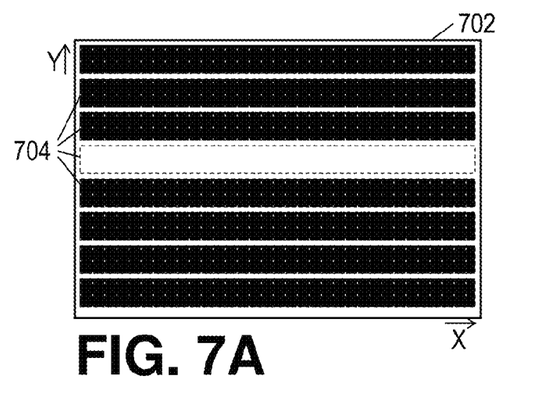
FIG. 7A shows an illustrative multiplex integrated computational element ("ICE"

FIG. 7A shows an illustrative ICE 702 of the multi-layered contrasting-refractive index variety. The illustrated ICE 702 is a multiplex device having different multi-layered structures over different image regions 704, but it is also contemplated that there may be only a single region 704 over the entire substrate surface. The regions 704 are continuous across the width of the device. Hereafter this type of region is described as "row-oriented". There is no horizontal spatial dependence to the ICE, meaning that, when employed as ICE 522 in FIG. 5A, each of the image fringes is processed based solely on their wavelengths. Nevertheless, the fidelity of the fringe measurement is increased by the suppression of irrelevant wavelength intensities (and hence the spatial fringes irrelevant to the fluid property measurement). Note that this ICE embodiment can be positioned nearly any here in the optical path.

The use of different ICE structures in corresponding row-oriented regions enables different ICE templates to be applied simultaneously. As the number of regions increases, however, the size of each region decreases correspondingly, reducing the total tight intensity associated with each measurement. In some embodiments, this loss may be compensated by lengthening the measurement time.

When the image is captured by a detector 530 (FIG. 5A) such as a ICCD (intensified charge coupled device), it is digitized and suitable for digital signal processing. (Other image capture detectors would also be suitable.) As previously mentioned, the processing may include combining measurements from different rows (albeit, different rows within the same region 704) to increase the signal to noise ratio, and may further include a spatial Fourier transform to derive the spectral content of the ICE-filtered outgoing beam. Such processing can be done using a software or firmware programmed general purpose processor, or an application specific integrated circuit. Fourier transform processing of the weighed or unweighted spatial pattern would allow for a system that uses SH-ICE to gather spectral data in-situ for calibration or re-calibration.

In most cases, however, it is expected that a Fourier transform would not be required, but rather the information in each row could be combined (averaged or summed) together to obtain a single value representative of the ICE-specific measurement (e.g., an analyte concentration). Such a measurement can be performed using software or hardware (e.g., an appropriately wired detector) or, as indicated in FIG. 5B, a minor or lens 524 that focuses the information from each row onto a row-associated point, yielding a one dimensional line. An array of photodetectors 540 may be provided along the line to enable each photodetector 540 acquire a row-associated measurement. Because the imaging array is now only one-dimensional, it can be further simplified to, a single photodetector 540 and a scanning mirror. The photodetector 540 can take the form of a photodiode, a thermal detector (including thermopiles and pyroelectric detectors), a Golay cell, or a photoconductive element. Cooling can be employed to improve the signal-to-noise ratio of the photodetector 540.

Whether the recombining of spatial fringe information is done optically (FIG. 5B) or electronically (FIG. 5A, after image capture by detector 530), signal to noise ratio may be improved by combining the measurements associated with all of the rows in a given region 704.

In FIGS. 5A and 5B, ICE 522 operates on the transmitted light. The systems can be readily modified to employ the reflected light, as indicated in FIG. 5C. ICE 526 has a wavelength-dependent reflectivity to provide the desired spectral weighting on the fringes that reach detector 530. Still other system embodiments measure both the transmitted and reflected light to achieve even higher performance. However, a similar performance is achievable with a multiplex ICE 702 having a regions 704 with complementary ICE templates, or by employing at least one 'reference' region that is weighted to a constant value (e.g. neutral density) or left as an unweighted (clear) region.

Figure 7B:
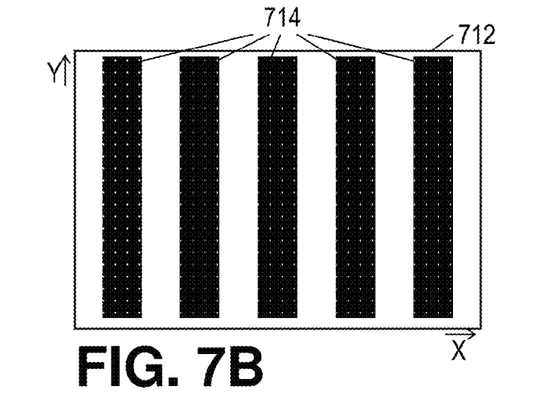
FIG. 7B shows an illustrative spatially-dependent ICE.

FIG. 7B shows an alternative ICE 712 that employs a spatial dependence to provide the desired spectral weighting. It employs regions that are continuous across the height of the device, i.e., along the y-axis, Hereafter, this type of region is described as "column-oriented". Because the spatial dependence corresponds to selected fringes, the wavelength selectivity of the regions can be relaxed. Indeed, some contemplated embodiments employ a mask that equally attenuates all wavelengths in that region of the beam. However, it is believed that the best efficiency will be achieved when at least some wavelength selectivity is combined with at least some spatial dependence, and the highest degree of performance should be achievable when the both the geometry and wavelength selectivity are carefully tailored to the desired measurement.

Figure 7C:
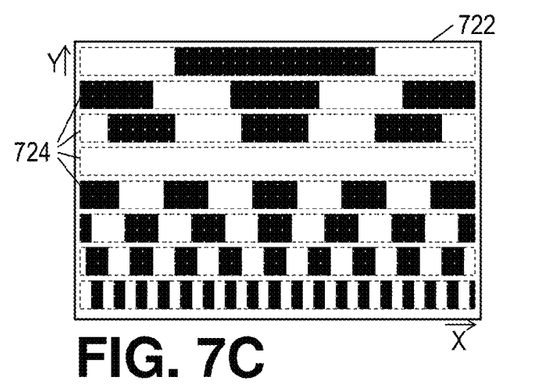
FIG. 7C shows an illustrative multiplex spatially-dependent ICE.

FIG. 7C shows an illustrative multiplex ICE 722 in which each row-oriented region 724 employs a spatially-dependent ICE structure. As before, the use of multiplexing enables multiple simultaneous measurements, though it does so by corresponding reducing the light intensity available for each measurement.

An alternative to a multiplex ICE is the use of multiple ICES that can be sequentially positioned in the light path, e.g., with the use of a rotating filter wheel. As yet another alternative, the ICE can be dynamically changed, e.g., with a programmable acousto-optic ICE (for changeable wavelength dependence) or a programmable electro-optic ICE (for changeable spatial dependence). Dynamically changeable ICEs may use individually controllable pixels of a liquid crystal tunable filter or an acousto-optical tunable filter. Other programmable ICEs include but are not limited to DLP or other types of MEMS based devices.

Figure 8:
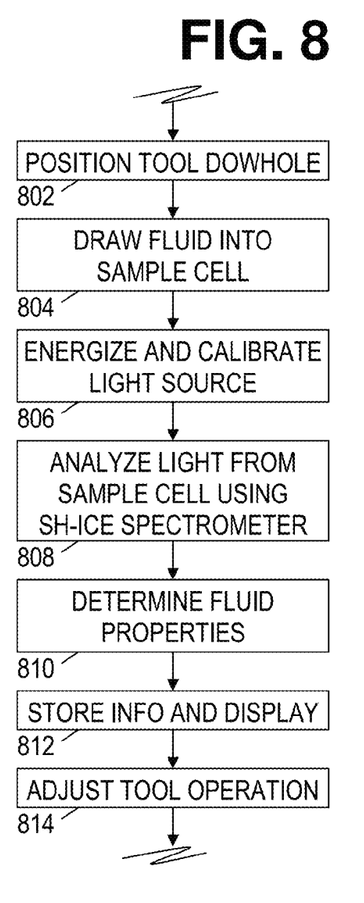
FIG. 8 is a flowchart of an illustrative downhole fluid analysis method.

FIG. 8 is a flowchart of an illustrative downhole fluid analysis method. It includes operations represented by blocks shown and described in sequential order, but this sequence is solely for explanatory purposes. In practice, the operations may be performed concurrently or, if sequential, may be performed in a different order or asynchronously.

In block 802, the driller positions the fluid analysis tool downhole, e.g., in a wireline sonde or a LWD collar. In block 804, fluid (e.g., from the formation) is drawn into a sample cell. In block 806, the light source is energized and calibrated, in some embodiments, the calibration is performed by measuring light received from the source via a path that bypasses the fluid sample, A measurement correction may be derived from this measurement. In addition, or alternatively, a feedback signal may be derived from a measurement based on the output from the light source and used to adjust the light intensity applied to the fluid sample.

In block 808, the tool illuminates the fluid sample with light from the source and analyzes the transmitted, reflected, or scattered light using a SH-ICE spectrometer, As discussed previously, the spectrometer obtains measurements indicative of fluid properties such as analyte concentrations. In block 810, these measurements are processed, either by the tool itself or by a surface facility, to derive the fluid properties. Illustrative properties include amount and type of hydrocarbons (e.g., fractions of saturated, aromatics, resins, and asphaltenes), amount and type of gas phase (e.g., $CO_2$, $H_2S$, etc.), amount and type of liquid phase (e.g., water cut), PVT properties (including bubble point, gas-to-oil ratio, density variation with temperature), concentrations of compounds such as concentration of treatment fluid, and amount of contamination (e.g., drilling fluid) in formation fluid sample.

In block 812, the tool and/or the surface facility communicates and stores the derived information. Contemporaneously, or later, the information is displayed to a user, preferably in the form of a log. In block 814, the operation of the tool is optionally adjusted in response to the measurement, e.g., by terminating a pumping operation when the contamination level falls below a predetermined threshold.

The SH-ICE embodiments shown in FIGS. 5A-5C employ a series of discrete optical elements arranged along an optical path, which may further include additional mirrors, lenses, apertures, switches, filters, sources, and detectors. Some contemplated embodiments employ an integrated ("monolithic") light path component. The integrated component provides reduced sensitivity to temperature changes, pressure changes, vibrations, and shock. A solid block of transparent material (e.g., quartz, sapphire, zinc selenide) is used as the body of the integrated component. Mirror gratings 518, 520, beam splitter 516, also made of the same material, ICE 522. (or ICE 526), and focusing element 524, are fused or otherwise attached to this body without any air gaps to maintain the alignment and spacing of the components over a wide range of temperature, pressure, vibration, and shock conditions.

Some tool embodiments, rather than being fluid analyzers, analyze a solid that is visible through a window or aperture, such as a core sample or a portion of the borehole wall adjacent to the tool. In such embodiments, the tool tracks the motion of the tool relative to the solid, associating the measurements with time and/or position to construct an image of the sample's surface.

Various techniques to maximize the quality of the measurements would be known to one of ordinary skill in the oil field industry and can be employed. For example, the tool may be outfitted with a reservoir of a reference fluid for downhole calibration of the system and for compensating for contamination on the windows of the flow cell. Detector cooling or temperature compensation can be used Co minimize the effects of temperature drift in the electronics.

Various other features can be incorporated into the tool. For example, scattered light can be analyzed to determine the size distribution of particles entrained in a fluid flow. An ultraviolet light source can be included to induce fluorescence in the material, which fluorescence can be analyzed to aid in determining composition of the sample.

The spectrometer designs and methods disclosed herein may be used in technologies beyond the oil field including, for example, the food and drug industry, industrial processing applications, mining industries, or any field where it may be advantageous to quickly determine a spectrally-related characteristic of a material. These and other variations, modifications, and equivalents will be apparent to one of ordinary skill upon reviewing this disclosure. It is intended that the following claims be interpreted to embrace all such variations and modifications where applicable.

What is claimed is:

1. A spectral analysis tool that comprises:
   a light source that illuminates a sample;
   a detector;
   an optical path that couples light that has interacted with the sample to the detector;
   a dispersive two-beam interferometer that transforms light propagating along the path into spatial fringe patterns associated with corresponding wavelengths; and
   an integrated computational element (ICE) that adjusts a spectral weighting of light propagating along the optical path.

2. The tool of claim 1, wherein the ICE has a programmable wavelength dependent attenuation.

3. The tool of claim 1, wherein the ICE employs spatially-dependent masking to adjust the spectral weighting based on a spatial dependence of the spatial fringe patterns.

4. The tool of claim 3, wherein the ICE has a programmable spatial dependence.

5. The tool of claim 3, wherein the ICE further employs wavelength dependent masking.

6. The tool of claim 5, wherein the wavelength dependence is programmable.

7. The tool of claim 3, wherein the ICE is a multiplex device employing multiple different row-oriented spectral weighting regions to provide multiple adjustments to the spectral weighting.

8. The tool of claim 1, wherein the ICE employs multiple different row-oriented spectral weighting regions to provide multiplex adjustments to the spectral weighting.

9. The tool of claim 1, further comprising a focusing element that recombines one or more rows of spatial fringe pattern information at row-associated points.

10. The tool of claim 9, wherein the detector comprises an array of detectors that capture row-associated combined intensity measurements at the row-associated points.

11. The tool of claim 1, wherein the detector acquires a two-dimensional image of spectral-weight-adjusted spatial fringe patterns, and wherein row-oriented spatial fringe pattern information is combined electronically.

12. The tool in claim 1, wherein detector acquires a two-dimensional image of spectral-weight-adjusted spatial fringe patterns, and wherein row-oriented spatial fringe pattern information is Fourier transformed electronically.

13. The tool of claim 1, wherein the spectral analysis tool is integrated into a downhole wireline or logging-while-drilling instrument package.

14. The tool of claim 13, wherein said sample includes fluid drawn from a formation.

15. The tool of claim 13, wherein the sample includes a portion of a borehole wall.

16. The tool of claim 13, wherein the sample includes fluid from a borehole.

17. A spectral analysis method that comprises:
    directing light from a light source to illuminate a sample;
    transforming light from the sample into spatial fringe patterns using a dispersive two-beam interferometer;
    adjusting a spectral weighting of the spatial fringe patterns using an integrated computation element (ICE);
    detecting combined fringe intensities derived from spectral-weight-adjusted spatial fringe patterns; and
    deriving at least one property of the sample.

18. The method of claim 17, wherein said detecting includes focusing spectral-weight-adjusted spatial fringe patterns into combined fringe intensities.

19. The method of claim 17, wherein said operations of directing, transforming, adjusting, focusing, and detecting are performed in a downhole tool.

20. The method of claim 19, further comprising modifying operation of the downhole tool based on said property.

21. The method of claim 17, wherein said adjusting includes applying a spatially-dependent mask to the spatial fringe patterns.

22. The method of claim 21, wherein the spatially-dependent mask further applies a wavelength-dependent attenuation.

23. The method of claim 17, wherein said adjusting includes applying different masks in multiple row-oriented regions.

24. The method of claim 17, wherein said detecting includes:
    sensing spectral-weight-adjusted spatial fringe patterns with a two-dimensional array of detectors; and
    electronically combining measurements along a row dimension to obtain the combined fringe intensities.

25. The method of claim 24, further comprising further comprising applying a spatial Fourier transform to the sensed spectral-weight-adjusted spatial fringe patterns.

26. The method of claim 17, wherein the downhole sample is a fluid drawn from a port seated against a borehole wall.

27. The method of claim 17, wherein the sample is a borehole fluid or a portion of a borehole wall.

28. The method of claim 17, wherein the property is at least one of: a contamination level, a quantity of at least one fluid type, and a concentration of at least one substance.

\* \* \* \* \*